US012239372B2

(12) United States Patent
Lamba et al.

(10) Patent No.: US 12,239,372 B2
(45) Date of Patent: Mar. 4, 2025

(54) FOCUS STACKING FOR RETINAL IMAGING (71) Applicant: Verily Life Sciences LLC, South San Francisco, CA (US)

(72) Inventors: Dhruv Lamba, Mountain View, CA (US); Sam Kavusi, Menlo Park, CA (US)

(73) Assignee: Verily Life Sciences LLC, Dallas, TX (US)

(*) Notice: Subject to any disclaimer, the term of this patent is extended or adjusted under 35 U.S.C. 154(b) by 0 days.

(21) Appl. No.: 18/230,073

(22) Filed: Aug. 3, 2023

(65) Prior Publication Data

US 2023/0389789 A1 Dec. 7, 2023

Related U.S. Application Data

(63) Continuation of application No. 17/489,670, filed on Sep. 29, 2021, now Pat. No. 11,766,170, which is a
(Continued)

(51) Int. Cl.
*A61B 3/00* (2006.01)
*A61B 3/10* (2006.01)
(Continued)

(52) U.S. Cl.
CPC .......... *A61B 3/0025* (2013.01); *A61B 3/0008* (2013.01); *A61B 3/10* (2013.01);
(Continued)

(58) Field of Classification Search
CPC ....... A61B 3/0025; A61B 3/0008; A61B 3/10; A61B 3/112; G06T 5/73; G06T 5/50;
(Continued)

(56) References Cited

U.S. PATENT DOCUMENTS 7,290,882 B2 11/2007 Collins et al.
7,506,982 B2 3/2009 Yahagi et al.
(Continued)

FOREIGN PATENT DOCUMENTS

CN 101172035 5/2008
JP 2005137584 A 6/2005
(Continued)

OTHER PUBLICATIONS

Motto et al., "All-in-Focus Imaging Technique Used to Improve 3D Retinal Fundus Image Reconstruction," SAC'15, Proceedings of the 30th Annual ACM Symposium on Applied Computing, 2015 ACM, 6 pages.
(Continued)

*Primary Examiner* — Wyatt A Stoffa
*Assistant Examiner* — Mitchell T Oestreich
(74) *Attorney, Agent, or Firm* — Christensen O'Connor Johnson Kindness PLLC (57) ABSTRACT

A system for imaging a retina of an eye includes a first lens for positioning proximate to the eye; a light source positioned to illuminate the eye when the system is aligned with the eye; an image sensor adapted to capture a retinal image of the retina through the first lens; an aperture disposed along an optical path extending from the image sensor and passing through the first lens; and a processing apparatus communicatively coupled to the image sensor and the light source, wherein the processing apparatus includes logic that when executed by the processing apparatus causes the system to perform operations including: illuminating the eye with the light source and capturing the retinal image with the image sensor.

22 Claims, 7 Drawing Sheets

Related U.S. Application Data continuation of application No. 16/046,265, filed on Jul. 26, 2018, now Pat. No. 11,160,449.

(60) Provisional application No. 62/551,708, filed on Aug. 29, 2017.

(51) Int. Cl.
  *A61B 3/11* (2006.01)
  *G06T 5/50* (2006.01)
  *G06T 5/73* (2024.01)

(52) U.S. Cl.
  CPC ........... *A61B 3/112* (2013.01); *G06T 5/50* (2013.01); *G06T 5/73* (2024.01); *G06T 2207/10152* (2013.01); *G06T 2207/20216* (2013.01); *G06T 2207/30041* (2013.01)

(58) Field of Classification Search
  CPC . G06T 2207/10152; G06T 2207/20216; G06T 2207/30041
  USPC ......................................................... 351/206
  See application file for complete search history.

(56) References Cited

U.S. PATENT DOCUMENTS

| | | | |
|---|---|---|---|
| 2001/0041884 A1* | 11/2001 | Frey | A61F 9/00806 606/5 |
| 2004/0207811 A1 | 10/2004 | Elsner | |
| 2012/0188356 A1 | 7/2012 | Jolma et al. | |
| 2013/0285885 A1 | 10/2013 | Nowatzyk et al. | |
| 2016/0249804 A1 | 9/2016 | Wang | |
| 2017/0082858 A1 | 3/2017 | Klug et al. | |
| 2017/0098117 A1 | 4/2017 | Stoker | |

FOREIGN PATENT DOCUMENTS

| | | |
|---|---|---|
| JP | 2009294719 A | 12/2009 |
| JP | 2012213555 | 11/2012 |
| JP | 20124653 | 7/2013 |
| JP | 2013144579 | 7/2013 |
| WO | 2015132775 A1 | 9/2015 |
| WO | 2017/079333 A1 | 5/2017 |
| WO | 2017/123702 A1 | 7/2017 |

OTHER PUBLICATIONS

Saine, "Focusing The Fundus Camera: A Clinical Approach," Journal of Ophthalmic Photography, vol. 14, No. 1, Sep. 1992, pp. 7-24.
Tong et al., "Simulation of Light Field Fundus Photography," stanford.edu/class/ee367/Winter2017/Tong_Melanson_ee367_win17_report.pdf, 6 pages.
Winn et al., "Factors affecting light-adapted pupil size in normal human subjects," Investigative Ophthalmology and Visual Science, Mar. 1994, vol. 35, No. 3, pp. 1132-1137.
International Search Report and Written Opinion from the International Searching Authority mailed Dec. 6, 2018 for International Application No. PCT/US2018/047605, filed Aug. 22, 2018, 8 pages.
Extended European Search Report, mailed Apr. 13, 2021, in corresponding European Patent Application No. 18851279.2, 6 pages.
Japanese Decision of Grant in corresponding Japanese Patent Application No. 2020-506329, mailed Feb. 15, 2021, 3 pages.
Chinese Office Action, mailed Nov. 25, 2021, in corresponding Chinese Patent Application No. 201880056822.8, 7 pages.
Chinese Office Action, mailed Apr. 19, 2022, in corresponding Chinese Patent Application No. 201880056822.8, 7 pages.
Chinese Decision of Rejection, mailed Aug. 2, 2022, in corresponding Chinese Patent Application No. 201880056822.8, 5 pages.
Office Action mailed Jul. 2, 2020, issued in corresponding U.S. Appl. No. 16/046,265, filed Jul. 26, 2018, now U.S. Pat. No. 11,160,449, 27 pages.
Final Office Action mailed Jan. 11, 2021, issued in corresponding U.S. Appl. No. 16/046,265, filed Jul. 26, 2018, now U.S. Pat. No. 11,160,449, 22 pages.
Notice of Allowance mailed Jun. 30, 2021, issued in corresponding U.S. Appl. No. 16/046,265, filed Jul. 26, 2018, now U.S. Pat. No. 11,160,449, 32 pages.
Office Action mailed Mar. 30, 2023, issued in corresponding U.S. Appl. No. 17/489,670, filed Sep. 29, 2021, 44 pages.
Notice of Allowance mailed May 5, 2023, issued in corresponding U.S. Appl. No. 17/489,670, filed Sep. 29, 2021, 40 pages.
Supplemental Notice of Allowability mailed May 24, 2023, issued in corresponding U.S. Appl. No. 17/489,670, filed Sep. 29, 2021, 6 pages.

* cited by examiner

FOCUS STACKING FOR RETINAL IMAGING

REFERENCE TO RELATED APPLICATION

This application is continuation of U.S. Ser. No. 17/489,670 filed Sep. 29, 2021, which is a continuation of U.S. Ser. No. 16/046,265 filed Jul. 26, 2018, which claims the benefit of U.S. Application No. 62/551,708, filed on Aug. 29, 2017, the contents all of which are incorporated herein by reference.

TECHNICAL FIELD

This disclosure relates generally to imaging technologies, and in particular, relates to retinal imaging.

BACKGROUND INFORMATION

Retinal imaging is a part of basic eye exams for screening, field diagnosis, and progress monitoring of many retinal diseases. A high fidelity retinal image is important for accurate screening, diagnosis, and monitoring. Bright illumination of the posterior interior surface of the eye (e.g., retina) through the pupil improves image fidelity while often creating optical aberrations or image artifacts, such as lens flare. Lens flare is a phenomenon where light scatters off of interior components of a lens system due to internal reflections, refractive index changes at various internal boundaries, imperfections, or otherwise. This scattered light shows up in the retinal image as lens flare, which is deleterious to the image quality. The brighter the illumination, the more pronounced the lens flare, which undermines the goal of improving image fidelity. Other image artifacts may arise due to corneal reflections or iris reflections from misalignment with the pupil.

BRIEF DESCRIPTION OF THE DRAWINGS

Non-limiting and non-exhaustive embodiments of the invention are described with reference to the following figures, wherein like reference numerals refer to like parts throughout the various views unless otherwise specified. Not all instances of an element are necessarily labeled so as not to clutter the drawings where appropriate. The drawings are not necessarily to scale, emphasis instead being placed upon illustrating the principles being described.

DETAILED DESCRIPTION

Embodiments of an apparatus and method for focus stacking for retinal imaging are described herein. In the following description numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Pupil dilation is an inconvenient component of retinal imaging. Even after the patient's pupils are fully dilated (a time consuming process in itself), the bright flash needed to image the retina forces the patient to blink, and the flash is generally very uncomfortable for the patient. Moreover, the large aperture provided by the increased pupil diameter, while good for maximizing light entering the eye for imaging, has the disadvantage of making the depth of field very shallow. Thus, only a small portion of the retina can be imaged at a time. Conversely, it is difficult to image a retina with a contracted (small) pupil: only a small amount of light travels to (and is reflected off of) the retina, and small misalignment of the light source and eye can result in corneal reflection. The instant disclosure remedies these suboptimal aspects of retinal imaging through focal stacking.

The eye's pupil is a relatively fast optical control system (e.g., a biomechanical aperture) that adjusts its diameter based on, at least in part, changes in illumination. Accordingly, the incident illumination of the iris can be ramped-up slowly (as opposed to blasting it with flash) while simultaneously imaging the iris at each "f-stop"—the ratio of the system's focal length to the diameter of the entrance pupil—to exploit a technique called "focal stacking" or "focus stacking". Focal stacking produces an image with a larger depth of field (i.e., the distance between the nearest and farthest objects in a scene that appear acceptably in-focus in the image). One of ordinary skill in the art having the benefit of the present disclosure will appreciate that pupil size also changes depending on the scene that is viewed. Therefore, in some embodiments, a scene may be used as a stimulus, while the retina may be illuminated and imaged using the infrared spectrum (single or multiple bands). In some embodiments, the eye may be illuminated with just infrared light or may be illuminated with a combination of infrared and visible light.

In focal stacking, several images containing the same subject (each with an in-focus portion of the subject) are combined so that the entire subject is in focus. It is appreciated by one of ordinary skill in the art having the benefit of the present disclosure that combining images here may include stacking (i.e., combing multiple images taken at different focus distances to give a resulting image with a greater depth of field than any of the individual source images), stitching (i.e., combining multiple photographic images with overlapping fields of view to produce a segmented panorama or high-resolution image), blending (i.e. combing a background image and foreground image giving the appearance of partial transparency), a combination thereof, or other types of image combination. In one embodiment, stacking may include a pixel-to-pixel alignment of the stacked image frames. In another or the same embodiment, stacking includes each image frame being stacked overlapping with another image frame being stacked by at least 25% of an area of the image frame. Here, several images of an iris can be captured with an image sensor, and the in-focus components of the image can be combined to create a composite image of the iris with a large depth of field.

An additional novel aspect of the techniques disclosed herein is that point illumination (rather than a light source that emits an annular ring) may be used to image an undilated pupil (e.g., not chemically dilated by physician). This enables the retina to be illuminated even when the pupil is contracted. Moreover, the retinal camera system disclosed here has a much higher frame rate (>240 frames/s) than traditional fundus cameras, and can allow imaging of several different "f-stops" in a very short burst of time. Since capture time is short, the probability of motion within that time frame decreases. Less motion in the series of images produces a higher quality composite image. Additionally, the intensity or emission time of the point illumination source may be varied to compensate for pupil shrinkage (e.g., as the pupil gets smaller the light source emits more, or brighter, light so more light is reflected from the interior of the eye into the camera).

It is appreciated that by employing the systems and methods disclosed here, it is possible to condense otherwise bulky retinal imaging systems into smaller devices. Smaller devices allow more people access to medical care, since at a minimum, costs associated with transport, delivery, and maintenance of the device are reduced.

Figure 1:
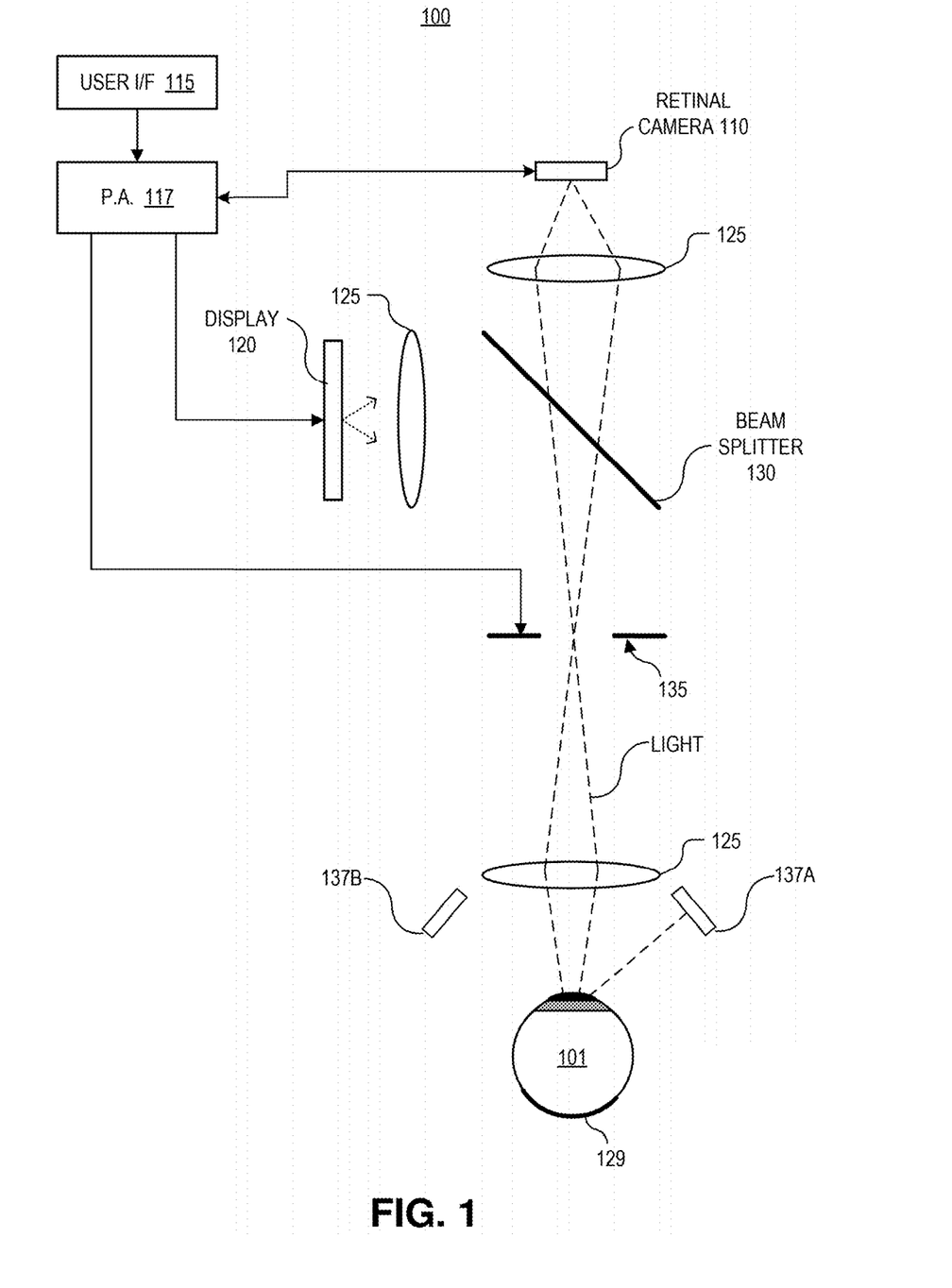
FIG. 1 illustrates a system for imaging a retina in an eye, in accordance with an embodiment of the disclosure.

FIG. 1 is a diagram illustrating retinal imaging system 100, in accordance with an embodiment of the disclosure. The illustrated embodiment of retinal imaging system 100 includes aperture 135, retinal camera 110, processing apparatus 117, user interface 115, display 120, light source (including light emitting diodes 137A and 137B), and an optical relay system that includes lenses 125, and beam splitter 130. It is appreciated that retinal imaging system 100 may be used to image other portions (other than the retina) of the interior of an eye, in accordance with the teachings of the present disclosure.

In the depicted embodiments, aperture 135 is physically positioned in the optical path of light from the retina to retinal camera 110 (which includes an image sensor), and operates as a stop to block many off-axis deleterious reflections that may otherwise reach retinal camera 110. However, in other embodiments, aperture 135 may be positioned in other locations, and additional apertures 135 may be added to the system. For example, there may be an aperture 135 that is conjugate to the retina and not allow light coming from other places. In the illustrated embodiment, the retinal images are passed through aperture 135 to retinal camera 110. In one embodiment, aperture 135 is coated with one or more optical films (e.g., dichroic coatings) to substantially pass light with wavelengths below 900 nm (i.e., to operate as a low-pass filter) while substantially reflecting light above 900 nm to facilitate the use of infrared (IR) gaze tracking. In one embodiment, an iris camera (not illustrated) is laterally disposed to aid IR gaze tracking. An iris camera may operate to track gross movements of eye 101, such as blinking and gaze tracking, by tracking or imaging the iris and/or the pupil of eye 101.

Beam splitter 130 is positioned to pass a portion of the light of retinal images to retinal camera 110 while reflecting display light output from display 120 to eye 101. The display light may include a fixation target or other visual stimuli to aid retinal alignment during imaging. In other words, display 120 is coupled to processing apparatus 117 to display an image positioned for the eye to look at (focus on) while a beam of light (e.g., from diodes 137A/137B) illuminates the retina. Additionally, as shown, other intermediate optics (e.g., lenses 125) may be disposed between the image sensor and aperture 135.

In some embodiments, beam splitter 130 is more transmissive than reflective. In one embodiment, beam splitter 130 is approximately 90% transmissive and 10% reflective. Other reflectance/transmittance ratios may be implemented. Lenses 125 are provided throughout system 100 to provide image and light focusing in the optical paths. User interface 115 provides a mechanism to commence burst image capture. In one embodiment, user interface 115 is a button, but may also include a touch screen or the like, to communicate a variety of states/statuses of imaging system 100 to a user of the system.

As shown, a light source with a plurality of light emitting diodes (LEDs), e.g., LEDs 137A and 137B, is positioned to illuminate the retina of eye 101 with one or more beams of light. In the depicted embodiment, LEDs 137A and 137B are located near eye 101 so that the light from the diodes does not travel through other optics in the system to reach eye 101. However, the light source may be disposed anywhere in system 100, in accordance with the teachings of the present disclosure. In the depicted embodiment, individual LEDs (e.g., 137A and 137B) in the plurality of LEDs are located in different locations, relative to eye 100, to shine the beam of light on a different location of the retina 129 by activating the individual LEDs at different times. For example, LED 137A may turn on and illuminate one portion of retina 129, then LED 137A may be turned off and LED 137B may be turned on to illuminate a different potion of retina 129. Alternatively or additionally, a single LED may be able to move to focus light in different locations.

An image sensor (e.g., included in retinal camera 110, which may have a frame rate of at least 200 frames per second) is positioned to receive the light reflected off of retina 129, and output a sequence of images (e.g., one at a time, in groups, or all at once) including images of the retina. Aperture 135 is positioned between eye 101 and retinal camera 110, and is shaped to block at least some of the light reflected off of a cornea of eye 101 from reaching the image sensor. This may prevent unwanted image noise, since reflection may cause luminance values that result in saturation of the image pixels in the image sensor. Processing apparatus 117 is coupled to the image sensor (e.g., physically included in, or wired to, retinal camera 110) to receive the sequence of images from the image sensor. The sequence of images may include 10 or more images, but may include more images such as 40 or 50 images to provide an oversampled data set. Processing apparatus 117 includes logic that when executed by the processing apparatus causes the processing apparatus to perform a variety of operations. For example, processing apparatus 117 may combine individual images in the sequence of images to form a composite image, and the composite image may have a larger depth of field than the depth of field of the individual images in the sequence of images.

In a different or the same embodiment, processing apparatus 117 may also be coupled to the light source to change a level of illumination output from the light source and directed at retina 129. When the level of illumination output from the light source is changing, the processing apparatus 117 may instruct the image sensor to capture the sequence of images. Thus, individual images in the sequence of images have a different depth of field since, as the level of illumination is changing, the diameter of the pupil of eye 101 is changing, which creates a different aperture size for the optical system. Put another way, the individual images in the sequence of images have a different depth of field as a result of a width of the pupil increasing or decreasing in size from the changing level of illumination. Thus, the pupil is acting as an aperture in system 100.

In another or the same embodiment, processing apparatus 117 further includes logic to remove a first set images (e.g., poor quality images) from the sequence of images. This first set of images is not included the individual images used to form the composite image. In some embodiments, the first set of images may include overexposed images having a luminance value (e.g., an average luminance value across all pixels, or sets of pixels, in the image) greater than a first threshold luminance value, or underexposed images having a luminance value less than a second threshold luminance value. In some examples, the images in the first set may not be clearly resolved for other reasons such as the image being too blurry (e.g., because the image sensor moved during capture), the images not containing an image of the retina (e.g., because the subject moved during image capture), or the like. Images may be removed via manual selection or by automated selection (e.g., using high pass/low pass filters to remove images with luminance values that are too high or too low, and/or or using a machine learning algorithm to remove images not including a retina, or the like). Once high-quality images are selected, and the low-quality images removed, the high quality images may be combined using focal stacking methods such as edge detection, feature detection, or Fourier analysis.

Figure 2:
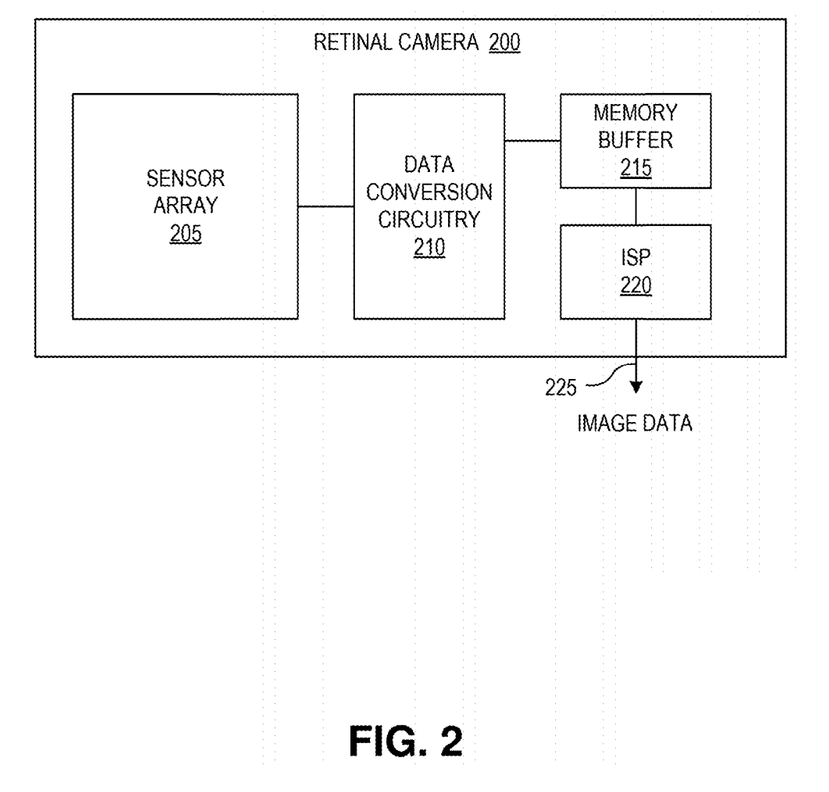
FIG. 2 is a functional block diagram of a retinal camera including an integrated image signal processor, in accordance with an embodiment of the disclosure.

FIG. 2 is a functional block diagram of a retinal camera 200 including an integrated image signal processor 220 (e.g., one embodiment of processing apparatus 117 of FIG. 0.1), in accordance with an embodiment of the disclosure. Retinal camera 200 is one possible implementation of retinal camera 110 of FIG. 1. The illustrated embodiment of retinal camera 200 includes a two-dimensional image sensor array 205, data conversion circuitry 210, a memory buffer 215, an integrated image signal processor (ISP) 220, and an output port 225.

During operation, two-dimensional image data (e.g., retinal images) is acquired by sensor array 205 and converted from the analog domain to the digital domain by data conversion circuitry 210. The image data may be acquired at a high frame rate (e.g., 24, 48, 60, 240, 1000 frames per second) and stored into memory buffer 215. ISP 220 operates on the buffered retinal image frames to identify useable or defect regions, annotate the regions of interest in the image frames, and/or combine the useable regions into high quality, composite retinal images. Accordingly, in one embodiment, some of the image processing tasks described above may be off-boarded to ISP 220 from processing apparatus 117 of FIG. 1. ISP 220 may be considered a logical subcomponent of processing apparatus 117 of FIG. 1.

Figure 3:
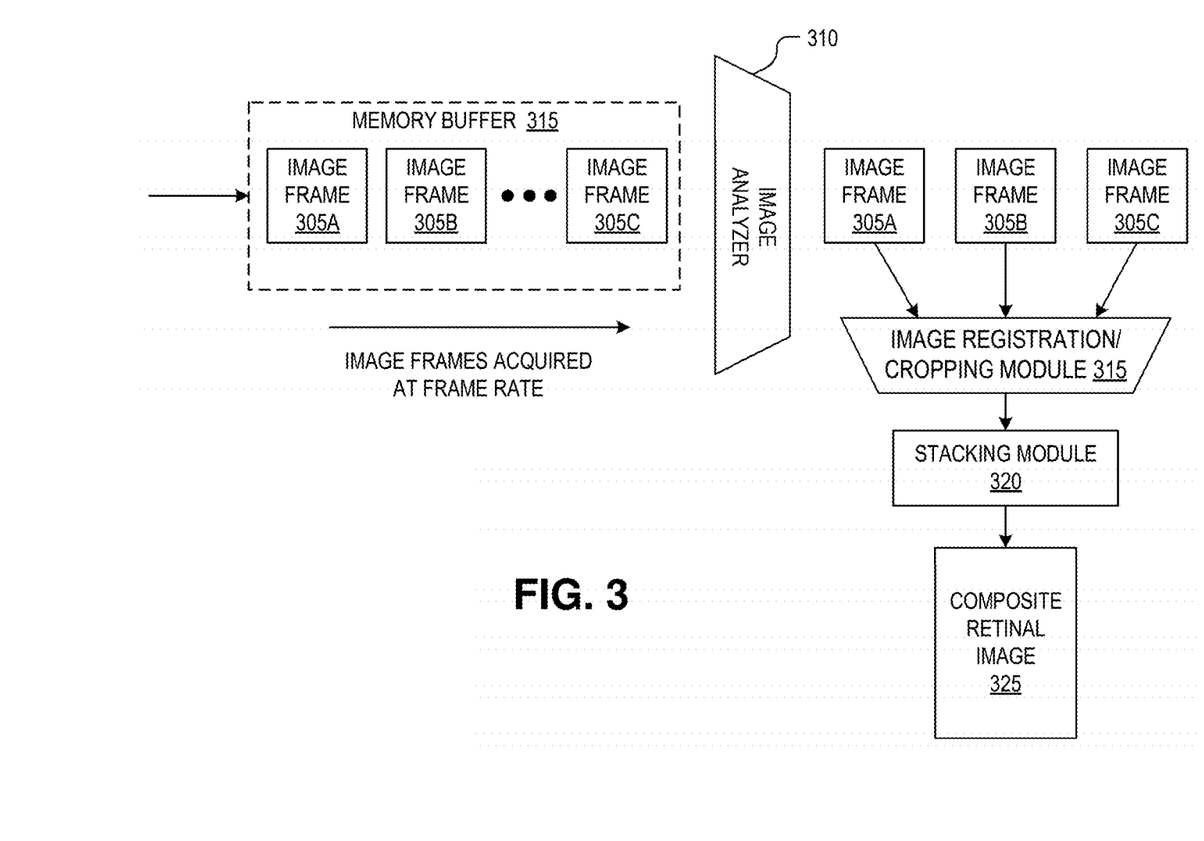
FIG. 3 is a block flow diagram illustrating image processing by a retinal camera including an integrated image signal processor, in accordance with an embodiment of the disclosure.

FIG. 3 is a block flow diagram illustrating image processing by retinal camera 200 of FIG. 2 that leverages the benefits of having the integrated ISP 220 to acquire high quality composite retinal images, in accordance with an embodiment of the disclosure. As illustrated, image frames 305A-350C of retina (e.g., retina 129 of FIG. 1) are acquired by sensor array 205 at a high frame rate, converted into the digital domain by data conversion circuitry 210, and buffered into memory buffer 215. An image analyzer 310 is executed by ISP 220 to analyze the buffered retinal images 305 (a sort of preprocessing) to determine which portions of images frames 305A-305C are of sufficient quality and which are of insufficient quality due to unacceptable image artifacts. For example, image analyzer 310 may analyze image frames 305A-305C for blurred portions, portions that do not have sufficient contrast to be useful, are washed out, and/or include unacceptable corneal or iris reflections, or lens flare. Image portions that are deemed unacceptable are flagged unacceptable (e.g., marked or annotated) while image portions that are deemed acceptable are flagged as such. The image frames are then registered to each other (e.g., pixel-to-pixel alignment), cropped to a common field of view by image registration/cropping module 315, and then combined by stacking module 320 into a single composite retinal image 325. Stacking module 320 may combine images to generate high dynamic range images with a large depth of field. In other embodiments, image frames 305 are simply combined without analysis and/or annotation of the individual image frames.

Figure 4:
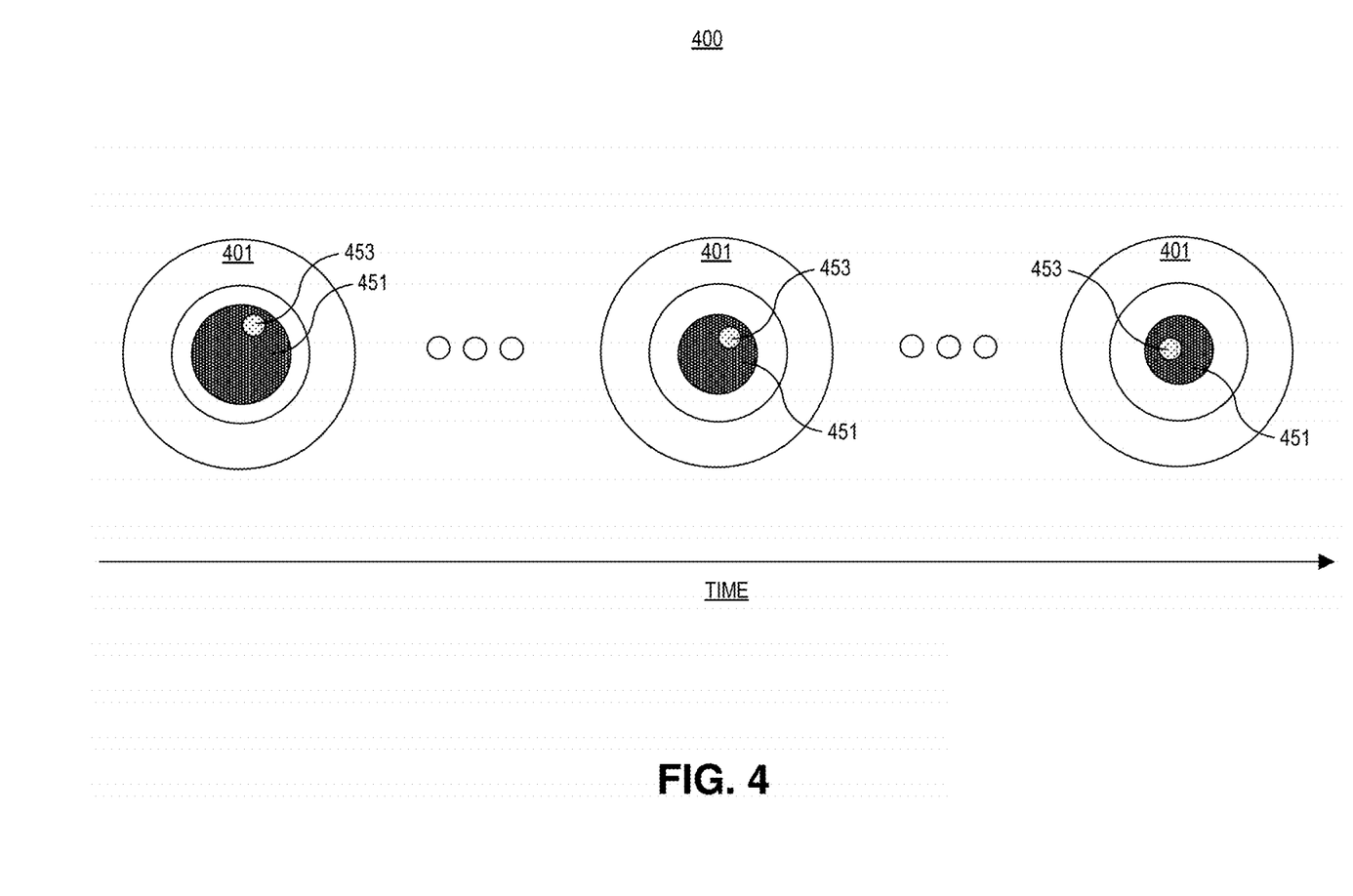
FIG. 4 illustrates illuminating an eye with a column of light, in accordance with an embodiment of the disclosure.

FIG. 4 illustrates illuminating an eye 401 with a beam of light 453, in accordance with an embodiment of the disclosure. As shown, an LED or other illumination source may shine beam of light 453 into pupil 451 of eye 401. In the illustrated embodiment, the beam of light is not annular; the entire beam is packed with photons to produce a dot (e.g., an illuminated point of any shape) on the retina of eye 401. In other words, the beam of light 453 illuminates a dot-shaped area on the retina, and the entire dot-shaped area receives photons from the light source. In some embodiments, beam of light 453 is emitted from LEDs and is substantially collimated, has a first width that is less than a width of a human pupil. In some embodiments the substantially collimated beam of light is formed using at least one of a laser, an aperture, or lens optics. In some embodiments, the dot-shaped point on the retina may be superior to annular illumination to reduce glare from different points around the eye when capturing the images. This may result in fewer over exposed or washed-out images in the sequence of images.

In the depicted embodiment, pupil 451 is progressively shrinking in size because beam of light 453 is increasing in intensity as a function of time. By changing a level of illumination output from the light source, the width of pupil 451 also changes. The image sensor may then capturing a sequence of images as the level of illumination output from the light source changes, and the images in the sequence of images have a different depth of field in response to the width of the pupil changing. It is appreciated that while the intensity of light could get brighter (higher intensity) with time (and thus contract the pupil), in other embodiments, the light could get progressively dimmer (decreasing intensity) with time (and thus expand the pupil). One of ordinary skill in the art having the benefit of the present disclosure will appreciate that a number of different sequences of light intensity changes may yield images with different focal points which may be combined to form a composite image. For example, the light from light source could get brighter, then dimmer, then brighter again. Or conversely, the light may get dimmer, then brighter, then dimmer again.

Figure 5:
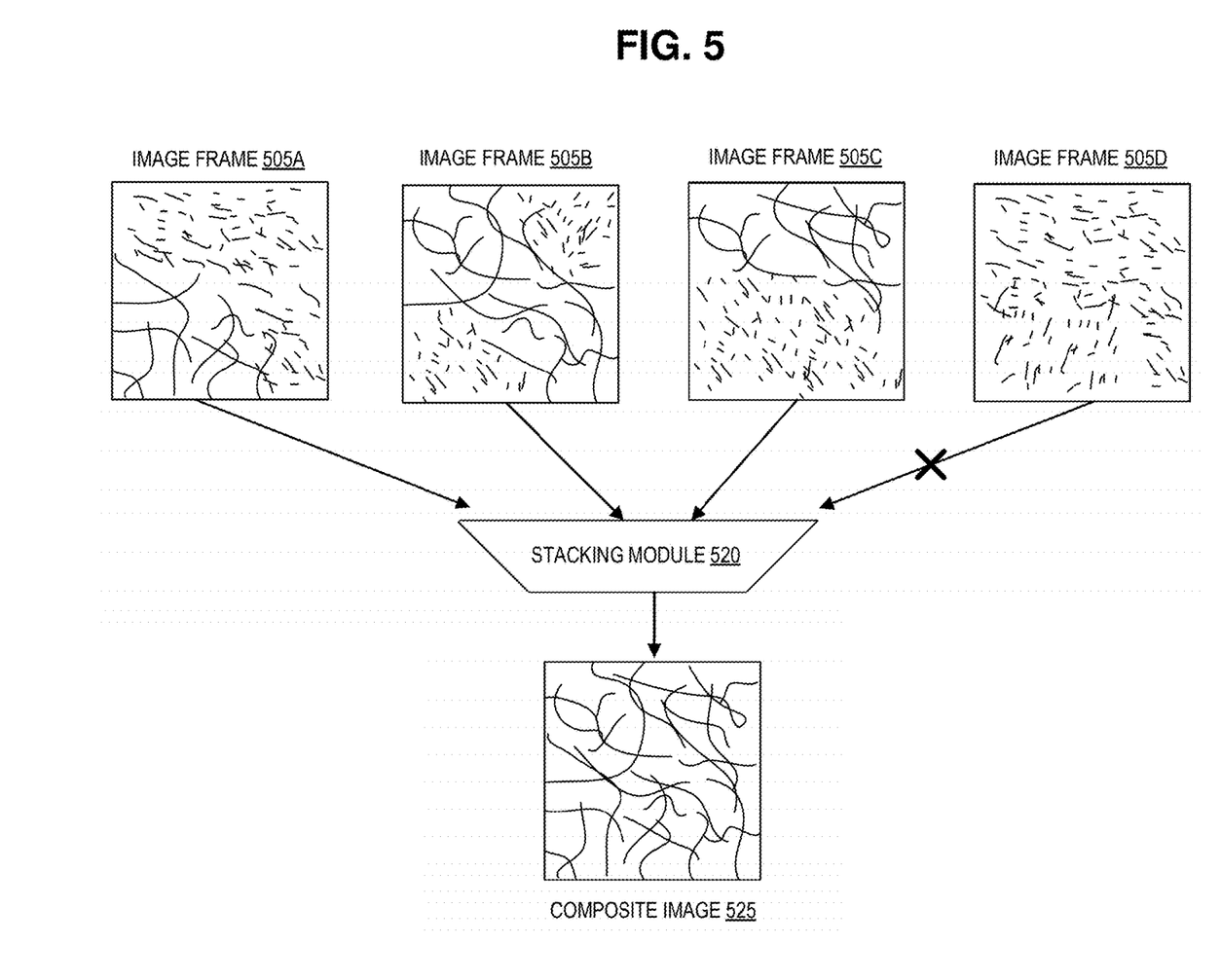
FIG. 5 illustrates focal stacking images of a retina, in accordance with an embodiment of the disclosure.

FIG. 5 illustrates focal stacking images of a retina or another part of an interior of an eye, in accordance with an embodiment of the disclosure. As shown, four image frames (505A-505D) of a retina are captured with an image sensor. Long lines represent fully resolved veins and other anatomical structures in/on the retina; short dashed lines represent out-of-focus or washed out portions of the image. As shown, the lower left hand corner of image frame 505A is fully resolved, but the rest of the image is not. Similarly, the middle portion (extending from the upper left-hand corner of the frame to the bottom right-hand corner) of image frame 505B is in focus and fully resolved, but the rest of image frame 505B is not. The upper right-hand corner of image frame 505C is in focus, but the rest of the image is not. Lastly, image frame 505D is out of focus and contains no useful information. Accordingly, image frame 505D is removed, and not sent to stacking module 520 for use in composite image 525. The rest of image frames 505A-505C are sent to stacking module 520 to be combined into a single high-resolution composite image 525 with a large depth of field. In one embodiment, images may be combined using edge detection, feature detection, or Fourier analysis.

Figure 6:
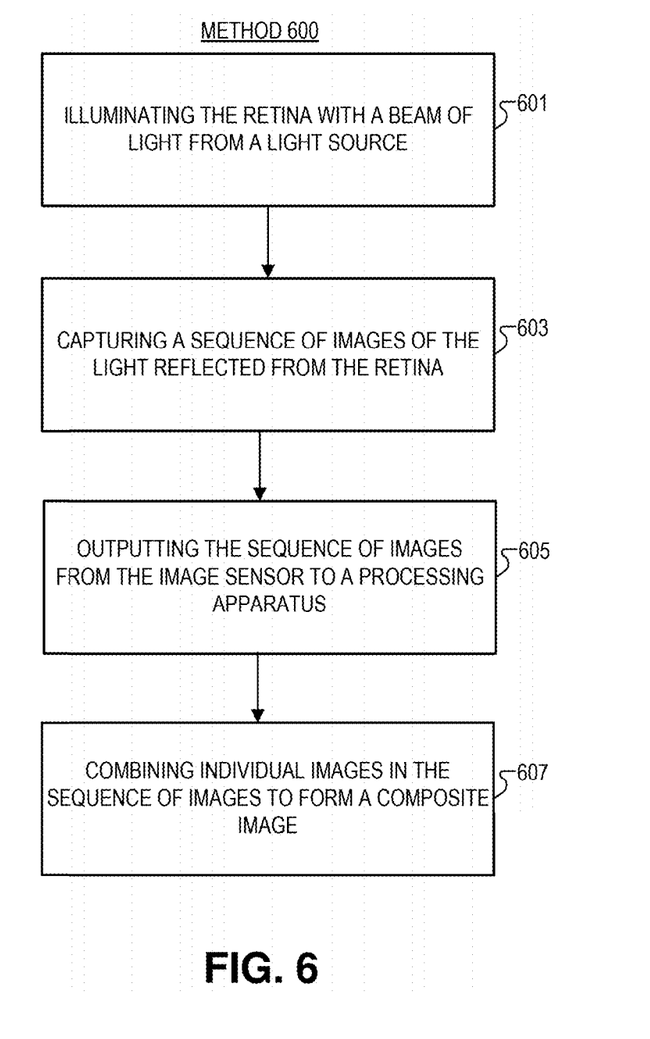
FIG. 6 illustrates a method of imaging a retina in an eye, in accordance with an embodiment of the disclosure.

FIG. 6 illustrates a method 600 of imaging a retina in an eye, in accordance with an embodiment of the disclosure. One of ordinary skill in the art having the benefit of the present disclosure will appreciate that blocks in method 600 may occur in any order and even in parallel. Moreover, blocks may be added to, or removed from, method 600 in accordance with the teachings of the present disclosure. Method 600 may be used to image other portions of the interior of the eye including, but not limited to, the retina. For example, portions of the eye, in in front of, or behind the retina may be imaged using this technique and the systems disclosed herein.

Block 601 shows illuminating the retina with a beam of light from a light source. As described above, the beam of light may have a width that is less than a width of a pupil of a human eye. It is appreciated that the eye may be undilated since the device and methods disclosed may use the undilated pupil as an aperture. Moreover, this eliminates the cumbersome and uncomfortable step of dilating a patient's eye.

In some embodiments illuminating the retina with the beam of light includes using a substantially collimated beam of light emitted from a plurality of LEDs or plurality of laser diodes. Moreover, the illuminated portions of the retina may include one or more dot-shaped areas on the retina, where the entire one or more dot-shaped areas receive photons from the light source. In other words, the illumination in these embodiments may not be annular.

In some embodiments, it may be necessary to block at least some of the light reflected off of a cornea of the eye from reaching the image sensor with an aperture disposed between the eye and the image sensor. This allows for more of the captured images to be of high enough quality to form the composite image. Aperture may also block unwanted reflections from portions of the eye other than the cornea.

Block 603 illustrates capturing, with an image sensor, a sequence of images of the light reflected from the retina. This may happen contemporaneously with changing a level of illumination output from the light source. Changing the level of illumination changes the pupil diameter, and allows for multiple images with different depths of field to be captured.

Block 605 depicts outputting the sequence of images from the image sensor to a processing apparatus, where the sequence of images includes images of the retina. Images may be transferred by wire or wirelessly (e.g., over the internet, or local area network). The processing apparatus may be part of the image sensor or camera, or may be included in another discrete piece of hardware. Processing apparatus may also be implemented in software and/or hardware, and contained in a single device or distributed across multiple devices (e.g., on multiple severs).

Block 607 shows combining, with the processing apparatus, images in the sequence of images to form a composite image having a larger depth of field than a depth of field of each of the images in the sequence of images. It is appreciated that the depth of field of each of the images corresponds to the width of the pupil when each of the images is captured. As described above, prior to combining the images, the processing apparatus may remove a first set images that may have image artifacts, glare, over/underexposure, from the images used to form the composite image. After the poor-quality images are removed, the processing apparatus may combine the images using a focus stacking technique, where the in-focus portions of the images are identified using at least one of edge detection, feature detection, or Fourier analysis.

Figure 7:
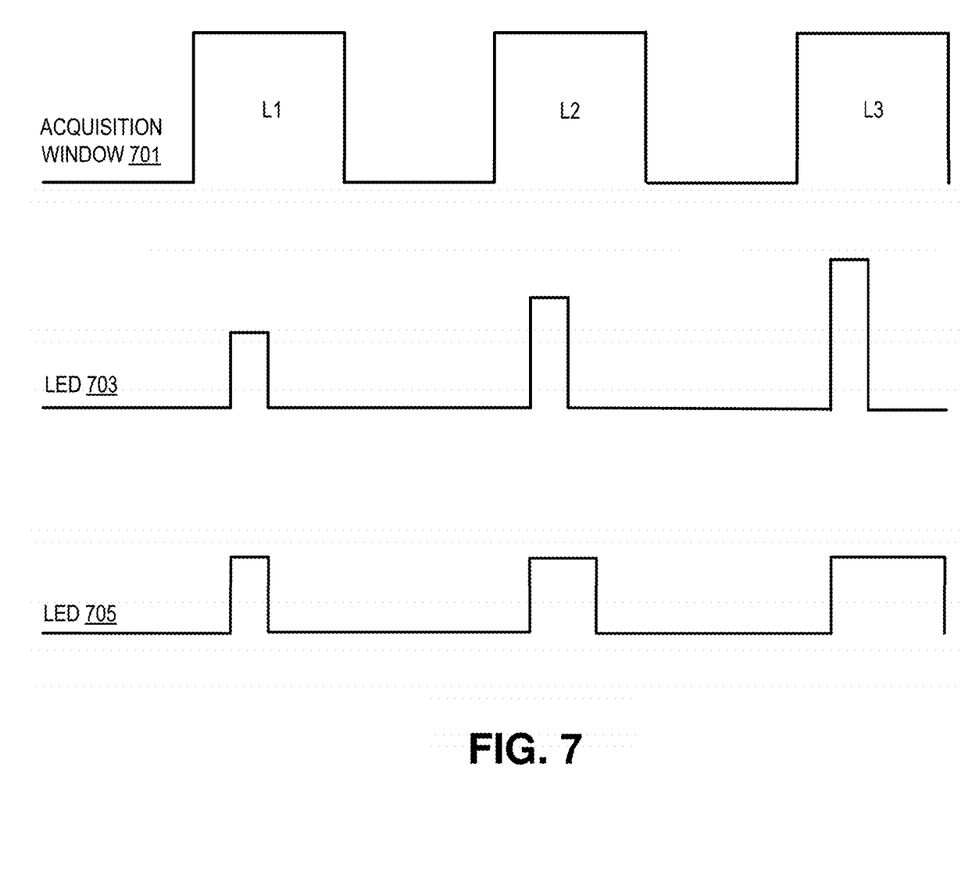
FIG. 7 depicts eye illumination patterns, in accordance with an embodiment of the disclosure.

FIG. 7 depicts eye illumination patterns, in accordance with an embodiment of the disclosure. As shown, during an image acquisition window 701 (also known as integration time, labeled L1, L2, L3, etc.) the light source (e.g., light emitting diodes 137A/137B of FIG. 1) may vary the level of illumination received by the eye by changing the intensity of the light, the on-time of the LED (e.g., the length of illuminating the eye), or both at the same time. For example, in LED output pattern 703 the intensity of the light increases with each successive acquisition window. Thus, as the pupil is shrinking in response to the light, the system can still capture an image since more light will be reflected from the retina. Similarly, in LED output pattern 703 the time that the light source is outputting the light is increasing with each successive acquisition window. Thus, as the pupil is shrinking in response to the light, the system can still capture an image since more light will be reflected from the retina. As shown, in some embodiments, the on-time of the light source is shorter than an integration time (e.g., the time the photodiodes are generating image charge) of the image sensor, while in other embodiments the integration time of the image sensor is less than the on-time of the light source. In some embodiments, the light source may remain on for multiple integration time periods, and change the intensity output gradually between each integration time period. Thus the total on-time of the light source is greater than the total integration time to capture the sequence of images. Alternatively, the light source may only be on during the integration time period, and for less than 50% of each integration time period, for example. In other embodiments, the light source may only be on for less than 40%, 30%, 20%, or 10% of each integration time period. Thus, in some embodiments, the total integration time to capture the sequence of images is greater than the total on-time of the light source when illuminating the retina.

In some embodiments, the integration time or capture window may be long and span multiple illumination events. Alternatively, the integration time may be relatively short, with charge being read from the photodiodes in the image sensor at several hundred frames per second to prevent image saturation.

It is appreciated that there are numerous patterns of light intensity, duration, and integration time (too many to be amenable for illustration), and that any pattern may be employed by the systems and methods disclosed here, in accordance with the teachings of the present disclosure.

The processes explained above are described in terms of computer software and hardware. The techniques described may constitute machine-executable instructions embodied within a tangible or non-transitory machine (e.g., computer) readable storage medium, that when executed by a machine will cause the machine to perform the operations described.

Additionally, the processes may be embodied within hardware, such as an application specific integrated circuit ("ASIC") or otherwise.

A tangible machine-readable storage medium includes any mechanism that provides (i.e., stores) information in a non-transitory form accessible by a machine (e.g., a computer, network device, personal digital assistant, manufacturing tool, any device with a set of one or more processors, etc.). For example, a machine-readable storage medium includes recordable/non-recordable media (e.g., read only memory (ROM), random access memory (RAM), magnetic disk storage media, optical storage media, flash memory devices, etc.).

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. A system for imaging a retina, the system comprising:
a first lens adapted for positioning proximate to an eye;
an image sensor positioned to capture a retinal image of the retina through the first lens;
a light source for generating illumination of the eye;
a display to output a fixation target;
a beam splitter disposed in an optical path extending from the image sensor through the first lens, the beam splitter positioned between the image sensor and the first lens and adapted to redirect the fixation target output from the display along the optical path out through the first lens for viewing by the eye, wherein the light source comprises a plurality of light emitting diodes (LEDs) disposed on either side of the optical path for illuminating different portions of the retina; and
a processing apparatus communicatively coupled to the image sensor, the light source, and the display, wherein the processing apparatus includes logic that when executed by the processing apparatus causes the system to perform operations including:
generating the fixation target;
illuminating the retina of the eye with the light source; and
capturing the retinal image with the image sensor while illuminating the eye.

2. The system of claim 1, further comprising:
a first aperture disposed between the image sensor and the first lens along the optical path, the first aperture surrounding the optical path and adapted to block off-axis reflections from the eye.

3. The system of claim 1, wherein the processing apparatus includes further logic that when executed by the processing apparatus causes the system to perform further operations including:
capturing a sequence of images of the retina while a diameter of a pupil of the eye is changing in response to the illumination from the light source, wherein at least some images of the retina in the sequence of images are acquired with different f-stops due to the diameter of the pupil changing in size during the illuminating; and
combining the at least some images in the sequence of images to form a composite image having a larger depth of field than any individual image in the sequence of images.

4. A system for imaging a retina, the system comprising:
a first lens for positioning proximate to an eye;
a plurality of light emitting diodes (LEDs) positioned to illuminate the eye, wherein the LEDs are positioned relative to the first lens such that light output from the LEDs does not pass through the first lens to illuminate the eye;
an image sensor positioned to capture a retinal image of the retina through the first lens;
an aperture disposed along an optical path extending from the image sensor and out through the first lens, the aperture surrounding the optical path and adapted to block off-axis reflections from the eye; and
a processing apparatus communicatively coupled to the image sensor and the LEDs, wherein the processing apparatus includes logic that when executed by the processing apparatus causes the system to perform operations including:
illuminating the eye with the LEDs; and
capturing the retinal image with the image sensor.

5. A system for imaging a retina of an eye, the system comprising:
a first lens for positioning proximate to the eye;
a light source positioned to illuminate the eye when the system is aligned with the eye, wherein the light source comprises a plurality of light emitting diodes (LEDs) each located in a different location to illuminate a different portion of the retina of the eye;
an image sensor adapted to capture a retinal image of the retina through the first lens;
an aperture disposed along an optical path extending from the image sensor and passing through the first lens, wherein the aperture surrounds the optical path; and
a processing apparatus communicatively coupled to the image sensor and the light source, wherein the processing apparatus includes logic that when executed by the processing apparatus causes the system to perform operations including:
illuminating the eye with the light source; and
capturing the retinal image with the image sensor.

6. The system of claim 5, wherein the LEDs are positioned relative to the first lens such that light output from the LEDs does not pass through the first lens prior to illuminating the eye.

7. The system of claim 6, wherein the LEDs are positioned laterally to the first lens.

8. The system of claim 5, wherein the light source comprises a plurality of light emitting diodes (LEDs) disposed on either side of the optical path.

9. The system of claim 5, wherein the aperture is positioned along the optical path between the image sensor and the first lens and adapted to block off-axis reflections from the eye.

10. The system of claim 5, further comprising:
an iris camera positioned to track movements of at least one of an iris or a pupil of the eye using infrared light.

11. The system of claim 5, further comprising:
a display coupled to the processing apparatus to output a display image in response to the processing apparatus.

12. A system for imaging a retina of an eye, the system comprising:
   a first lens for positioning proximate to the eye;
   a light source positioned to illuminate the eye when the system is aligned with the eye;
   an image sensor adapted to capture a retinal image of the retina through the first lens;
   an aperture disposed along an optical path extending from the image sensor and passing through the first lens, wherein the aperture surrounds the optical path;
   a display adapted to output a display image;
   a beam splitter disposed in the optical path between the first lens and the image sensor, the beam splitter adapted to redirect the display image output from the display along the optical path through the first lens for viewing by the eye, wherein the display image comprises visual stimuli to aid alignment of the retina to the image sensor; and
   a processing apparatus communicatively coupled to the image sensor, the display, and the light source, wherein the processing apparatus includes logic that when executed by the processing apparatus causes the system to perform operations including:
      illuminating the eye with the light source; and
      capturing the retinal image with the image sensor.

13. The system of claim 12, wherein the display image comprise a fixation target for the eye.

14. The system of claim 12, wherein the beam splitter is disposed along the optical path between image sensor and the aperture.

15. The system of claim 12, further comprising:
   a second lens disposed between the beam splitter and the image sensor; and
   a third lens disposed between the display and the beam splitter.

16. The system of claim 5, wherein the processing apparatus includes further logic that when executed by the processing apparatus causes the system to perform further operations including:
   capturing a sequence of images of the retina while a diameter of a pupil of the eye is changing in response to illumination from the light source, wherein at least some images of the retina in the sequence of images are acquired with different f-stops due to the diameter of the pupil changing in size during the illuminating; and
   combining the at least some images in the sequence of images to form a composite image having a larger depth of field than any individual image in the sequence of images.

17. The system of claim 16, wherein the processing apparatus includes further logic that when executed by the processing apparatus causes the system to perform further operations including:
   changing a level of illumination output from the light source and directed toward the retina, wherein the sequence of images are captured as the level of illumination output from the light source changes.

18. The system of claim 17, wherein the different f-stops are achieved in response to the diameter of the pupil in the eye increasing or decreasing in size from changing the level of illumination from the light source.

19. A system for imaging a retina of an eye, the system comprising:
   a first lens for positioning proximate to the eye;
   a light source adapted for illuminating the eye;
   an image sensor aligned to image the retina through the first lens;
   an aperture disposed along an optical path extending from the image sensor and out through the first lens, the aperture surrounding the optical path and adapted to block off-axis reflections from the eye; and
   a processing apparatus communicatively coupled to the image sensor and the light source, wherein the processing apparatus includes logic that when executed by the processing apparatus causes the system to perform operations including:
      illuminating the eye with the light source;
      burst capturing a plurality of retinal images of the retina with the image sensor;
      registering the retinal images to each other; and
      stacking the retinal images into a composite retinal image having a higher quality than an individual one of the retinal images.

20. The system of claim 19, wherein the higher quality comprises fewer defect regions or fewer image artifacts than the individual one of the retinal images.

21. The system of claim 19, wherein the burst capturing comprises capturing the retinal images at a rate of 24 frames per second or greater.

22. The system of claim 19, wherein the processing apparatus includes a memory buffer to buffer the retinal images and an integrated signal processor (ISP) adapted to analyze the retinal images buffered in the memory buffer to perform the registering and the stacking to generate the composite retinal image.

* * * * *